US006635680B2

(12) United States Patent
Mulye

(10) Patent No.: US 6,635,680 B2
(45) Date of Patent: *Oct. 21, 2003

(54) CONTROLLED RELEASE PELLET FORMULATION

(75) Inventor: Nirmal Mulye, Long Beach, NY (US)

(73) Assignee: Nostrum Pharmaceuticals, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/165,907

(22) Filed: Jun. 10, 2002

(65) Prior Publication Data

US 2002/0192285 A1 Dec. 19, 2002

Related U.S. Application Data

(63) Continuation of application No. 09/650,838, filed on Aug. 30, 2000, now Pat. No. 6,475,493.
(60) Provisional application No. 60/152,115, filed on Sep. 2, 1999.

(51) Int. Cl.[7] ........................ A01N 25/00; A61K 9/00; A61K 9/28; A61K 9/30
(52) U.S. Cl. ................. 514/964; 514/965; 424/400; 424/465; 424/474; 424/475
(58) Field of Search ................. 424/465, 400, 424/474, 475; 514/964, 965

(56) References Cited

U.S. PATENT DOCUMENTS

| | | |
|---|---|---|
| 3,957,523 A | 5/1976 | Ohno et al. |
| 4,083,949 A | 4/1978 | Benedikt |
| 4,282,233 A | 8/1981 | Vilani |
| 4,367,217 A | 1/1983 | Gruber et al. |
| 4,389,393 A | 6/1983 | Schor et al. |
| 4,432,966 A | 2/1984 | Zeitoun et al. |
| 4,438,091 A | 3/1984 | Grubber et al. |
| 4,568,559 A | 2/1986 | Nuwayser et al. |
| 4,623,588 A | 11/1986 | Nuwayser et al. |
| 4,659,716 A | 4/1987 | Villani et al. |
| 4,661,162 A | 4/1987 | Kurihara et al. |
| 4,728,512 A | 3/1988 | Mehta et al. |
| 4,728,513 A | 3/1988 | Ventouras |
| 4,756,911 A | 7/1988 | Drost et al. |
| 4,800,084 A | 1/1989 | Zerbe |
| 4,806,361 A | 2/1989 | Harrison et al. |
| 4,808,413 A | 2/1989 | Joshi et al. |
| 4,832,958 A | 5/1989 | Baudier et al. |
| 4,859,469 A | 8/1989 | Baudier et al. |
| 4,904,474 A | 2/1990 | Theeuwes et al. |
| 5,026,559 A | 6/1991 | Eichel et al. |
| 5,084,287 A | 1/1992 | Ghebre-Sellassie et al. |
| 5,169,638 A | 12/1992 | Dennis et al. |
| 5,202,128 A | 4/1993 | Morella et al. |
| 5,217,720 A | 6/1993 | Sekigawa et al. |
| 5,238,686 A | 8/1993 | Eichel et al. |
| 5,277,916 A | 1/1994 | Dwyer et al. |
| 5,330,766 A | 7/1994 | Morella et al. |
| 5,378,474 A | 1/1995 | Morella et al. |
| 5,472,710 A | 12/1995 | Klokkers-Bethke et al. |
| 5,496,561 A | 3/1996 | Okada et al. |
| 5,529,791 A | 6/1996 | Deboeck et al. |
| 5,540,945 A | 7/1996 | Ikushima |
| 5,800,836 A | 9/1998 | Morella et al. |
| 5,834,024 A | 11/1998 | Heinicke et al. |
| 5,837,379 A * | 11/1998 | Chen et al. .......... 424/465 |

* cited by examiner

Primary Examiner—Alton N. Pryor
(74) Attorney, Agent, or Firm—Scully, Scott, Murphy & Presser

(57) ABSTRACT

The present invention describes an aqueous pharmaceutical coating formulation which can be used for coating core elements containing one or more medicaments to achieve controlled release. The coated pharmaceutical formulation provides a release of medicaments in a controlled manner at highly acidic environment such as that of stomach and shows relatively faster release in media with basic pH such as that of the intestine. The coating composition is a heterogenous mixture which comprises (a) at least 75% by weight of a water insoluble polymer which is insoluble in both acidic as well as basic pH; and (b) 1 to 25% by weight of an enteric polymer which is substantially insoluble in water at a pH below 4.5 and which is substantially soluble in water at a pH between above about 6.0, said enteric polymer and water insoluble polymer being present in an amount effective to control-the release of said medicament. The pharmaceutical composition comprises a solid medicament present in effective amounts and the coating composition thereover.

16 Claims, No Drawings

CONTROLLED RELEASE PELLET FORMULATION

RELATED APPLICATION

The present application is a continuation of U.S. Patent Application U.S. Ser. No. 09/650,838, filed on Aug. 30, 2000 now U.S. Pat. No. 6,475,493, which is claiming priority of provisional application U.S. Ser. No. 60/152,115, filed on Sep. 2, 1999.

FIELD OF THE INVENTION

The present invention relates to a sustained release pharmaceutical composition and to a method of using and preparing same in order to control the rate of release and the site of release of the pharmaceutical composition.

BACKGROUND OF THE INVENTION

It is desirable in the treatment of a number of diseases, both therapeutically and prophylactically, to provide the active pharmaceutical ingredient in a sustained release form. Desirably, the sustained release form provides a controlled rate of release of a medicament over an extended period.

It is well known that well absorbed sustained release therapeutic drug dosage forms provide many advantages over conventional release dosage forms. The advantages include less frequent dosing of a medicament and resultant patient compliance, a more sustained drug blood level response, therapeutic action with less ingested drug and the mitigation of side effects. By providing a slow and steady release of the medicament over time, absorbed concentration spikes are mitigated or even eliminated by effecting smoother and more sustained blood level response.

Some sustained release pharmaceutical formulations are prepared such that they have a core containing the medicament or drug which is surrounded by a coating which controls the release of the drug or medicament.

A multi-particulate dosage form, especially those in which the core containing the medicament or drug is surrounded by one or more coatings, provides distinct advantages over a single component system such as a tablet since the release profile is more directly controlled by the amount of coating and the number of layers of coating. Moreover, it has the advantage of facilitating the preparation of the desired release profile from a combination of medicaments relative to the single tablet form. Although non-pH dependent polymers are often used for coatings to achieve a controlled release of active substances, they sometimes pose a problem because the release of the active substance is dependent on the solubility of the drug, and the solubility of some drugs, such as that of Verapamil hydrochloride, changes with pH. It is therefore desirable to formulate a coating which becomes more permeable as the pH is increased and the drug solubility thereof decreases.

Other coatings in pharmaceutical composition contain enteric polymers which are pH dependent. These enteric coatings are generally formulated from anionic polymers with pendent carboxyl groups which typically have a pKa of 4 to 6. Gastric fluids typically have pH values about two units below the pKa. For example, the pH value in the stomach of an ordinary person is normally between 1 and 3.5 and mostly between 1 and 2.5. Thus, in the low pH gastric fluids, only about 1% of the carboxyl groups ionize; 99% of the carboxyl groups are protonated and the carboxyl groups can form hydrogen bonds with each other and with other portions of the polymer. Thus, in these pH ranges in the stomach, enteric polymers are insoluble in the gastric fluid. The enteric polymer coating thus retains its integrity and provides a barrier to moisture. When the dosage form reaches the intestines, where the intestinal fluids have a higher pH, ionization of the carboxy group increases and the enteric material dissolves, the extent of this ionization being dependent upon the pH and the enteric coating used.

Thus, some drugs have an enteric soluble coating so as to effect release thereof in areas other than the stomach, whereby the pH values are higher. For example, the pH value in the small intestines is normally from 5 to 7; moreover, it is even higher as one goes up along the intestine and may reach 7–8 in the lower intestine. The pH value in the empty duodenum is about 6.5, although it is about 3.5 after a meal.

Some of the reasons for effecting release of the drug outside of the stomach are listed hereinbelow:

(1) prevention of decomposition of drugs that are unstable at pH values lower than a certain level;

(2) prevention of side effects brought about by the release of drugs in the stomach including irritation of the stomach wall by the drug;

(3) prevention of dilution of drug concentration in the intestines, attributable to disintegration of drugs in the stomach and their subsequent movement to the intestines; and (4) prolonged effect.

There are, in fact, various types of enteric coated drugs, depending upon their functional requirements, as the object of using them can be different. They thus can be divided into the following types:

(a) Those that do not release drugs in the stomach, i.e., these enteric-coated drugs do not undergo dissolution, dispersion or disintegration at the pH value in the stomach of an ordinary person, and the drug is not released in the stomach through the membrane of the preparation;

(b) Those that do not need to specify the site at which disintegration takes place; these preparation will not undergo dissolution, dispersion or disintegration at pH values below a specified value, and outside liquids will not permeate into such preparations through the membrane, but they do undergo dissolution, dispersions or disintegration at pH values higher than this specified value; or (c) Those that undergo dissolution, dispersion or disintegration at a specified site, particularly at a specified site in the intestines.

Unfortunately, the bioavailability of known enteric-coating preparations varies significantly at each administration between individuals or even in the same individual, both in terms of the quantity released and the rate of release of the active component. This inevitably gives rise to uncertainties as to the effectiveness of enteric-coating preparations. Moreover, it is a common observation that the average bioavailability of enteric coated preparations is lower than that of other preparations. This is partly because of variations in the pH in the digestive organs between individuals or in the same individual but at different times and partly because it is difficult to be certain that the enteric coat surrounding the medicament will dissolve, disperse or disintegrate sufficiently rapidly and with certainty in the digestive organs, particularly in the small intestine.

For example, if a drug is administered in a single enteric-soluble unit dosage (e.g., a tablet), which can be absorbed only in the upper small intestine, bioavailability will be 0% if, for any one of many reasons, the dose does not happen to disintegrate in the upper small intestine and, as a result, the drug may not be utilized at all. In order to avoid this risk, administration is sometimes effected by means of a large number of small unit doses (for example, a number of enteric soluble granules contained together in a conventional capsule). Administration in this way, however, means that at each administration, the bioavailability is the average of the bioavailabilities of the individual granules, which is therefore less than the theoretical maximum of 100%. Accordingly, although this expedient has the effect of ensuring that there is a reasonable likelihood that at least some of the active ingredient given with each administration is utilized, it does not improve the overall average bioavailability.

A suggestion to overcome these problems is described in U.S. Pat. No. 5,202,128 to Morella, et al., which discloses a pH-dependent sustained release pharmaceutical pellet composition for administration to a patient at a predetermined dosage and interval which comprises a core element containing a therapeutically effective amount of at least one active ingredient having an aqueous solubility of at least 1 in 30 and a coating on said core element which comprises:

(a) at least 35% by weight of a matrix polymer which is insoluble at a pH of from 1 to 7.5 and contributes to the control of the rate of release of the active ingredient in the stomach and intestines;

(b) from 1 to 30% of an enteric polymer which is substantially insoluble at a pH of from 1 to 4 sufficient to delay the release of the active ingredient in the stomach, but which is soluble at a pH of from 6 to 7.5 so as not to substantially delay release in the intestines; and (c) from 1 to 60% of a compound soluble at a pH of from 1 to 4, sufficient to enable initiation of release of the active ingredient in the stomach, said percentages being by weight based upon the total weight of components (a), (b) and (c); the ratio of the components (a), (b) and (c) in said coating being effective to allow the initiation of the release of the active ingredient in the stomach at a slow rate and to control the release in the intestines at a rate faster than that in the stomach such that a dose of the pellet composition delivers to the patient a therapeutically effective amount of the active ingredient over the course of said predetermined interval.

In U.S. Pat. No. 5,202,128, the coating requires all three components: the insoluble polymer, the enteric polymer and a compound soluble at a pH from 1 to 4. The third component, the soluble compound at pH from 1 to 4, is required; it is not optional. A coating comprised of the first two components alone prepared in accordance with the procedure described in U.S. Pat. No. 5,202,128 is so rigid and so strong that the coat will not dissolve, disperse or disintegrate sufficiently rapidly to release the medicament in effective concentrations while the pharmaceutical composition is in the gastrointestinal tract of the patient. The third component is thus required to initiate release of the drug in the stomach, that is, it helps to partially solubilize the coat so as to permit the initial release of the drug through the coat.

As taught by U.S. Pat. No. 5,202,128, the coat is homogenous, and it is this quality which partly attributes to strengthening of the coat. However, the present inventor has found that if the coat is not homogenous, but rather heterogenous, the coat is weaker, and the third component of the coating composition in U.S. Pat. No. 5,202,128 is not a necessary component.

More specifically, the present inventor has developed a controlled release pharmaceutical composition which comprises the active ingredient in a core element and a coating surrounding the core element which comprises a heterogenous mixture, the components therein comprising a water insoluble polymer which is insoluble in both acidic as well as basic pH and an enteric polymer which is essentially insoluble in water at a pH below 4.5 at 25° C. Thus, the present inventor has found a sustained release formulation in which the coating is required to contain only two components. The coating, however, may require an optional third ingredient to retard the initial release, said third component being a water soluble polymer. However, contrary to the coating composition in U.S. Pat. No. 5,202,128, which requires a third component to initiate release of the active ingredient in the stomach, the third component, if present, in the coating composition of the present invention is to prevent a rapid initial release in the stomach (known as a burst).

In accordance with the present invention, the coating composition, as a heterogenous mixture, is applied to the core using an aqueous vehicle in which the polymers are dispersed and/or mixed, and then the coating is dried to substantially remove the water contained in the coating composition. As described hereinbelow, in an aspect of the present invention, the heterogenous mixture comprises (a) a pH independent polymer present as a latex dispersion in water; (b) an enteric polymer, which is added thereto as a powder or latex dispersion or as a solution in weak base; and (c) optionally, a water soluble polymer, dissolved in aqueous solution.

SUMMARY OF THE INVENTION

Accordingly, the present invention is directed to a coating composition in a controlled release pharmaceutical composition comprising a mixture, said mixture comprising (a) at least 75% by weight of a water insoluble polymer which is insoluble in both acidic as well as basic pH and (b) 1 to 25% by weight of an enteric polymer which is substantially insoluble in water at a pH below 4.5, said coating composition being a heterogenous mixture. The present invention is also directed to a sustained release pharmaceutical composition comprising a core element containing a pharmaceutically effective amount of at least one active ingredient and a coating surrounding said core element, which coating comprises a mixture comprising:

(a) at least 75% by weight of a water insoluble polymer which is insoluble in both acidic as well as basic pH (pH independent polymer) and (b) 1 to 25% by weight of an enteric polymer which is substantially insoluble in water at a pH below 4.5, said coating composition being a heterogenous mixture.

The present invention is also directed to a method of treating a disease for which the medicament is effective comprising administering to the mammal in need of such treatment the controlled release pharmaceutical composition of the present invention. Another aspect of the present invention is directed to the method of making the controlled release pharmaceutical composition of the present invention.

DESCRIPTION OF THE INVENTION

An aspect of the present invention is directed to a coating composition in a controlled release pharmaceutical composition which comprises a mixture comprising an enteric polymer which is substantially insoluble in water at a pH less than 4.5 and a water insoluble polymer that is substantially insoluble in aqueous media in acidic or basic pH, said mixture being heterogenous. This coating composition surrounds a core containing the active ingredient and is a heterogenous mixture. Another aspect of the present invention is directed to a controlled release pharmaceutical composition comprising a core element comprising the medicament or drug and said coating. This controlled release formulation of the present invention is to be administered to mammals in need of the medicament in the formulation, wherein the medicament is present in the formulation in effective amounts.

By mammal, it is meant a vertebrae of the class Mammalia that is characterized by possession of hair and mammary glands. Examples include, inter alia, dog, cat, horse, pig, goat, cow, and human being. The preferred species of mammal to which the sustained release formulation of the present invention is to be administered is man.

The terms "sustained release" and "controlled release" are being used interchangeably. As used herein, they refer to the release of the active ingredient at such a rate that blood levels are maintained within the therapeutic range but below toxic levels over an extended period of time, e.g., 4 to 24 hours or even longer.

The term "bioavailability" as used herein refers to the extent-to which the active drug ingredient is absorbed from the pharmaceutical formulation and is available at the site of drug action.

The first component of the coating composition of the present invention is a water insoluble polymer which is substantially insoluble in aqueous solution in both acidic as well as basic pH. By substantially insoluble in aqueous solution in both acidic and basic pH, it is meant that the polymer is substantially insoluble in aqueous solution, regardless of the pH, i.e., its solubility in aqueous solution is independent of the pH. Thus, the first component is insoluble in both the gastric and intestinal fluids. It is preferred that the solubility of the water insoluble polymer at 25° C. is less than 0.001 g/l.

The insoluble polymer is any suitable pharmaceutically acceptable non-toxic polymer substantially insoluble in aqueous media, e.g., water, independent of the pH thereof. Thus, it is insoluble in the gastric fluid, i.e., at pH's less than 4 and is insoluble in the intestinal fluid, at pH's between 6.0 and 7.5 and at the various pH's between 4 and 6 at 25° C. It is also insoluble in water at pH's greater than 7.5 at 250° C. The polymer may be a cellulose ether, cellulose ester or cellulose ether-ester in which a part or all of the hydroxy groups on the cellulose skeleton are substituted. In view of the requirement that the insoluble polymer is substantially insoluble in both the gastric and intestinal fluids, these cellulose derivatives having a minimal number of hydrophilic substituents are preferred. Examples include ethyl cellulose, acetyl cellulose, nitrocellulose, and the like.

Other examples of insoluble polymers include lacquer, and acrylic and/or methacrylic ester polymers, polymers or copolymers of acrylates or methacrylates having a low quaternary ammonium content, or mixtures thereof and the like. Other examples include methylmethacrylate polymers e.g., EUDRAGIT RS® which is a water-insoluble film former based on neutral swellable methacrylic acid esters with a small proportion of trimethylammonioethyl methacrylate chlorides, the molar ratio of the quaternary ammonium groups to the neutral ester groups is 1:40 (~25 meq/100 g), EUDRAGIT RL® which is also a water insoluble, swellable film former based on neutral methacrylic acid esters with a small proportion of trimethylammonioethyl methacrylate chloride, the molar ratio of quaternary ammonium groups to the neutral ester group is 1:20 (corresponding to about 50 meq/100 g), EUDRAGIT NE®, which is a neutral methacrylic acid ester without any functional groups that forms a water insoluble film, and the like. The cellulose derivatives, especially, e.g., ethyl cellulose, is the most preferred.

The insoluble polymer comprises at least 75% by weight of the coating. It is more preferred that it comprises at least about 80% by weight of the coating by weight and most preferably at least about 85% of the coating by weight.

The other necessary component of the coating is the enteric polymer which is essentially insoluble in an aqueous media at a pH at 4.5 or less. In other words, it is substantially insoluble at 25° C. in an aqueous media at pH's of 4.5 or less, e.g., the pH's typically found in the gastric juices, but is soluble in aqueous solution in pH's greater than about 4.5, for example, in pH's typically found in the intestinal fluid. It is preferred that the solubility of the enteric polymer in aqueous media at pH of 4.5 or less at 25° C. is 0.001 g/l. However, the enteric polymer is soluble at a pH above about 6.0 and especially in the range from about 6.0 to about 7.5, i.e., the pH of the intestinal fluid, so as to permit release of the drug in the intestine and so as to not to substantially delay release therein.

The enteric polymer is non-toxic and includes any pharmaceutically acceptable enteric polymer which fits the above description, i.e., predominantly soluble in the intestinal fluid, but substantially insoluble in the gastric juices. Examples include polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L®, which is an anionic copolymer based on methacrylate and available as a powder (also known as methacrylic acid copolymer, type A (USP NF), methacrylic acid-methyl methacrylate copolymer, ethyl methacrylate-methylmethacrylate-chlorotrimethylammonium ethyl methacrylate copolymer and the like and mixtures thereof. Other examples include natural resins, such as shellac, Sandarac®, copal collophorium and mixtures thereof. These and other enteric polymers are described in U.S. Pat. No. 5,800,836, the contents of which are incorporated by reference, and these enteric polymers can also be utilized in the coating composition of the present invention. Other examples include synthetic resin bearing carboxyl groups. The methacrylic acid: acrylic acid ethyl ester 1:1 copolymer solid substance of the acrylic dispersion sold under the trade designation "Eudragit L-100-55" has been found to be suitable. The most preferred enteric polymers are PVAP, cellulose acetate butyrate, cellulose acetate propionate and cellulose acetate phthalate.

As indicated hereinabove, the enteric polymer is present in the coating composition of the present invention in amounts ranging from about 1% to about 25% by weight of the coating, more preferably from about 2 to about 25% by weight and even more preferably from about 2 to about 20% and especially from about 5% to about 20% and even more especially from about 5% to about 15% by weight of the coat and most preferably from about 8 to about 15% by weight of the coat. The enteric polymer, however, is preferably not present in amounts greater than 25% by weight of the coat.

Both the enteric polymer and the water insoluble polymer are present in effective amounts to form a film over the active ingredient that substantially retards the release of the medicament in aqueous solutions at a pH of 4.5 or less. It is preferred that the insoluble polymer and the enteric polymer are present in the coating composition in a weight ratio ranging from about 3:1 to about 20:1, respectively and more preferably from about 3:1 to about 15:1 and most preferably from about 4:1 to about 10:1.

It is believed, without wishing to be bound, that the water insoluble polymer and the enteric polymer interact to form a barrier over the core element containing the active ingredient to control the rate of release of the active component.

However, it is preferred that a third component also is present in the coat. The third component is an optional component, and is a water soluble polymer. The term "soluble" is being defined herein as in the USP, the contents of which are incorporated by reference.

The third component, which is optional, is substantially hydrophillic. Examples include hydroxy propylmethylcellulose (HPMC), polyvinyl providone (PVP), polysaccharides, such as gums, maltodextrins, and the like.

Without wishing to be bound, it is believed that there may be instances that when the first and second component interact, the barrier obtained therefrom has imperfections or holes, resulting from the incomplete coalescence of the latex particles. Moreover, it is believed, without wishing to be bound, that these imperfections and/or holes permit the diffusion therethrough of the active ingredient in an uncontrolled manner. The third component is added so that these "holes" are plugged. Thus, the third component, the soluble polymer, is present in an amount effective to further retard the release of the active component from the pharmaceutical composition, i.e., in an amount effective to plug the "holes". If present, the third component is present in an amount up to about 8% by weight of the coat and more preferably from about 0.1 to about 8% and more preferably from about 0.25 to about 6% even more preferably from about 0.5% to about 5% by weight of the coat and most preferably from about 3% to about 5% by weight of the coat. The present invention contemplates two different embodiments when the water soluble polymer is present. In one embodiment, the water soluble polymer is admixed with the-components in the coating composition and the coating composition forms a coat surrounding the central core containing the active ingredient. In a second embodiment, the pharmaceutical composition contains two coats. The coat immediately surrounding the central core comprises the soluble polymer. On top of that layer is the coating composition of the present invention with and preferably without any additional soluble polymer. In this embodiment, the coating composition of the present invention completely surrounds the first coat layer and forms a second coast layer.

The coating composition of the present invention may, if desired, contain other conventional additives in addition, such as plasticizers, film forming materials, film forming agents, polymer particles, surfactants, coloring agents, excipients, including fillers, such as talc, titanium dioxide or barium sulphate or antioxidants in order to improve the properties of the preparation, as is well known to the skilled artisan.

It is preferred that the coating composition of the present invention includes a wetting agent or emulsifying agent or defoaming agent. Examples include sodium lauryl sulfate, emulsifying wax, lecithin, polymethyl siloxane emulsion, cetostearyl alcohol, cetyl alcohol, glyceryl monostearate, sodium stearate, lanolin alcohols, polyoxyethylene sorbitan fatty acid esters, polyoxy ethylene stearates, propylene glycol alginate, stearyl alcohol, sorbitan esters and the like or a mixture thereof.

The coating may also contain such lubricants as talc, calcium stearate, colloidal silicon dioxide, magnesium stearate, zinc stearate, aluminum stearate, polyethylene glycol, glycerin, and the like or a mixture thereof.

It is important that the coating composition be heterogenous. More specifically, this coating composition is heterogenous with respect to the pH independent water soluble polymer and in most instances, with respect to the enteric polymer and reasonably homogenous with respect to the pH independent water insoluble polymer, the water soluble polymer, if present, and any other component which is present. Without wishing to be bound, it is believed that it is the heterogeneity of the coating composition that imparts the necessary characteristics to the coat. More specifically, it is essential that either the water insoluble polymer or the enteric polymer and more preferably both are present in particulate form and that they are not dissolved in the aqueous media used to prepare the coating composition. Thus, the resulting coating composition contains solid particles. It is preferred that the coating composition, when placed in water, has a solid content of at least about 5% and more preferably from about 5% to about 25% (w/w).

The coating composition of the present invention is prepared by dispersing and/or mixing the water insoluble polymer, the enteric polymer, the water soluble polymer, if present, and any other additional components in water until the components are evenly distributed therethrough. Preferably, they are mixed or dispersed in a mixer or homogenizer. Alternatively, the various components may be mixed with a stirrer until evenly distributed. Usually, they are mixed for four to five minutes. After mixing the components, the composition can be applied to the core, which is described hereinbelow. Preferably the insoluble polymers being used in this invention are latex dispersions of polymers in water based systems. More specifically, the coating material is prepared by mixing the enteric polymer material in an aqueous medium and adding thereto the insoluble polymer in a latex dispersion. The various components are mixed or dispersed until the various components are evenly distributed. The coating resulting therefrom is a heterogenous mixture or dispersion. The aqueous latex dispersions formed therefrom are heterogeneous systems, unlike those formed by dissolution of polymers in organic solvents. These dispersions can be better described as suspensions or emulsions. The coating is formed by fusion of these polymer droplets or particles. For certain types of coatings, viz., ethyl cellulose, heat is often applied after coating to achieve coalescence of these particles. In short, the coating obtained in accordance with this procedure tend to be more porous than those obtained by using organic solutions of the same polymer.

The coating composition of the present invention is present in an amount effective to retard the release of the active ingredient of the pharmaceutical composition. Preferably, it is present in at least 3% by weight of the core and more preferably from about 3% to about 15%, even more preferably from about 4% to about 10% by weight of the core and most preferably from 4% to about 8% of the core.

As described hereinbelow, the active ingredient is present in the core element. The active ingredient can be of any type of medication which acts locally in the mouth or acts systemically, which in the case of the latter, can be administered orally, to transmit the active medicament into the gastrointestinal tract and into the blood, fluids and tissues of the body. The pharmaceutical composition of the present invention may contain one active ingredient or more than one active ingredient.

Representative active medicaments include antacids, anti-inflammatory substances, coronary vasodilators, cerebral vasodilators, peripheral vasodilators, anti-infectives, psychotropics, antimanics, stimulants, anti-histamines, laxatives, decongestants, vitamins, gastro-intestinal sedatives, antidarrheal preparations, anti-anginal drugs, vasodilators, antiarrythmics, anti-hypertensive drugs, vasoconstrictors drugs useful to treat migraines, anticoagulants and antithrombotic drugs, anagesics, anti-pyretics, hypnotics, sedatives, anti-emetics, anti-nauseants, anticonvulsants, neuromuscular drugs, hyper- and hypoglycaemic agents, thyroid and antithyroid preparations, diuretics, antipasmodics, uterine relaxants, mineral and nutritional additives, antiobesity drugs, anabolic drugs, erythropoietic drugs, antiasthmatics, expectorants, cough suppressants, mucolytics, antiuricemic drugs and other drugs or substances acting locally in the mouth, such as topical anagetics, local anaesthetics, etc.

Typical active ingredients include gastro-intestinal sedatives such as metoclopramide and propantheline bromide; antacids such as aluminium trisilicate, aluminium hydroxide and cimetidine; anti-inflammatory drugs such as phenylbutazone, indomethacin, naproxen, ibuprofen, flurbiprofen, diclofenac, dexamethasone, predinisone and prednisolone; coronary vasodilator drugs such as glyceryl trinitrate, isosorbide dinitrate and pentaerythritil tetranitrate; peripheral and cerebral vasodilators such as soloctidilum, vincamine, naftidorofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotilline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfoxuccinate; nutritional supplements such as ascorbic acid, alpha tocopherol, thiamine and pyridoxine; antispasmodic drugs such as dicyclomine and diphenoxylate; drugs affecting the rhythm of the heart, such as verapamil, nifedipine, diltiazem, procainamide, disopyramide, bretylium toxylate, quinidine sulfate and quinidine gluconate; drugs used in the treatment of hypertension such as propranolol hydrochloride, guanethidine mono-sulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; anagesic drugs such as acetylsalicyclic acid, acetaminophen, codeine phosphate, codeine sulfate, oxydodone, dihydrocodeine tartrate, oxycodeinone, morphine, heroin, nalbuphine, butorphanol tartrate, pentazocine hydrochloride, cyclazacine, pethidine, buprenorphine, scopolamine and mefanamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland disfunction such as triodothyronine, thyroxine and propylthiouracil; diuretic drugs such as furosemide, chlorthalidone, hydrochlorthiazide, spironolactone and trimterene; the uterine relaxant drug ritodrine; appetite suppressants such as fenfluramine hydrochloride, phentermine and diethylproprion hydrochloride; anti-asthmatic and bronchodilator drugs such as aminophyline, theophyline, salbutamol, orciprenaline sulphate and terbutaline sulphate; expectorant drugs such as fuaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid; drug useful for treating Crohn's disease, e.g., 5-amino salicyclic acid, and the like.

Vitamins include such vitamins as vitamin A, vitamin D, vitamin B (d-α-tocopherol acetate, etc.), vitamin $B_1$, (dibenzoylthiamin, fursultiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), vitamin $B_{12}$ (hydroxocobalamin acetate, etc.); minerals such as calcium, megnesium, and iron.

The active ingredient may also be present as the pharmaceutically acceptable salt of any of the drugs mentioned hereinabove.

The active ingredient in the present invention, however, is preferably a drug that may be chemically unstable in acidic pH or may cause irritation of the gastric lining. Alternatively, the active ingredient is preferably a drug whose solubility decreases significantly with increasing pH or whose intended site of action or absorption is the small intestine, large intestine or colon, rather than the stomach. Additionally, a preferred drug for this formulation is one that is a pharmaceutically active orally acceptable ingredient having an aqueous solubility of approximately 1 in 30 or greater.

The active ingredient may be present in any suitable effective amount. The amount of active ingredient is dependent on the potency of the active ingredient and on the desired dosage strength and volume of a unit dose of the drug product. The active ingredient may be present in amounts of approximately 0.1 to 95% by weight, based on the total weight of the core element.

The active ingredient is surrounded by the coating; thus, it is at the core. The active ingredient is contained in the core element. The central core is produced by processes known in the art in which the active ingredient and other additive components, such as fillers, binders, lubricants and the like are subjected to various known processes, such as a process in which fine granule and granules are produced by wet or dry granulation, a process in which tablets are produced by direct compression tableting, a process in which granules and beads are produced by extrusion granulation, a process in which granules and beads are produced by extrusion granulation and subsequent treatment with a marumerizer, and the like.

The central core contains the active ingredient and other conventional additives such as plasticizers, excipients, binders, anti-oxidants, lubricant fillers, coloring agents, anti-oxidants, sweeteners, flavoring agents, preservatives and any other optional ingredients. These are then provided into any suitable unit dosage form, such as a tablet, capsule, pill, granule or powder to form the desired preparation. If the pharmaceutical composition is being prepared in the form of a tablet, a lubricant may additionally be and is preferably present in the pharmaceutical formulations of the present invention. "Lubricant", as used herein, refers to a material which can reduce the fraction between the die walls and the punch faces which occurs during the compression and ejection of a tablet. The lubricant prevents sticking of the tablet material to the punch faces and the die walls. As used herein, the term "lubricant" includes anti-adherents. The lubricant, if present, is present in lubricating effective amounts in the central core. Preferably, the lubricant is present in amounts ranging from about 0.1% to about 5% by weight and more preferably from about 0.5% to about 2% by weight of the core element. Examples of lubricants include stearate salts, e.g., alkaline earth and transition metal salts, such as calcium, magnesium and zinc stearates; stearic acid; polyethylene oxide; talc; hydrogenated vegetable oil; vegetable oil derivatives, and the like. In addition, if the unit dosage form is a tablet, the tablet may contain a combination of more than one type of lubricant. Other lubricants that also can be used include silica, silicones, high molecular weight polyalkylene glycol, e.g., high molecular weight polyethylene glycol, monoesters of propylene glycol, and saturated fatty acids containing about 8–22 carbon atoms and preferably 16–20 carbon atoms. The preferred lubricants are the stearate salts, especially magnesium and calcium stearate and stearic acid.

Regardless of the unit dosage form, excipients, such as plasticizers, for example, diethylphthalate (DEP), dibutyl sebacate, triethyl citrate, triacetin, vegetable and mineral oils, polyethylene glycol, maltodextrin and the like, may optionally be present. Preferably, the plasticizer, when present, is present in the pharmaceutical formulations of the present invention in amounts ranging from about 0.01% to about 25%, and more preferably from about 0.1% to about 10% and most preferably from about 1% to about 5% by weight of the core element.

Fillers, such as maltodextrin, sugar, lactose, and microcrystalline cellulose may also be present. They are preferably present in amounts ranging from about 2% to about 70% by weight of the core element.

Other optional ingredients that are also typically used in pharmaceuticals may also be present, such as coloring agents, preservatives (e.g., methyl parabens), artificial sweeteners, flavorants, anti-oxidants, and the like. Artificial sweeteners include, but are not limited to, saccharin sodium, aspartame, dipotassium glycyrrhizinate, stevia, thaumatin and the like. Flavorants include, but are not limited to, lemon, lime, orange and menthol. The colorants include, but are not limited to, various food colors, e.g., FD&C colors, such as FD&C Yellow No. 6, FD&C Red No. 2, FD&C Blue No. 2, food lakes and the like. Examples of anti-oxidants include ascorbic acid, sodium metabisulphite and the like. These optional ingredients, if present, preferably are present in amounts ranging from about 0.1% to about 5% by weight of the core element and most preferably less than about 3% (w/w) of the core element.

In a preferred embodiments, the central core is in the form of a pellet.

The pellet is prepared by layering a solution of suspension of the active ingredient on starter particles, i.e., an inert core material which is preferably a sphere, bead or seed and then coating the finished pellet with a functional layer to provide the necessary release characteristics. The starter particles or seeds can be any free flowing nonfriable granular material such as sucrose or lactose or can be crystals of the active ingredient which serve as starter seeds. Preferably, it is a sugar or starch sphere having an average diameter of from about 0.5 mm to about 1.5 mm.

In addition to the active ingredient or drug, the pellet also preferably contains a binder. A binder promotes adhesion of the drug to the beads and is present in binding effective amounts. Preferably, the binding agent is present in amounts of from about 0.1 to about 45% by weight of the core element and more preferably from about 0.1 to about 20% by weight and most preferably approximately about 3 to about 15% by weight, based on the total weight of the core element.

The binding agent may be any suitable type used in the pharmaceutical art. Suitable binders may be selected from polyvinyl-pyrrolidone, hydroxypropyl cellulose, hydroxypropyl methyl cellulose, sugars (e.g., glucose), acacia, carboxymethylcellulose sodium, dextrin, ethylcellulose, gelatin, pregelatinized starch, sodium alginate, zein, and the like or mixtures thereof. The binding agent may be provided in the form of a granulating solution. An aqueous or organic solvent may be included. Methanol, ethanol or mixtures thereof may be used as solvents.

Besides the active ingredient and a binder that promotes adhesion of-the drug to the starter seeds, the core may also contain antiadherents that prevent or minimize agglomeration during the layering process, and other ingredients such as surfactants, excipients, fillers, stabilizing agents, buffers, coloring, or flavoring agents which may be desirable depending on the physicochemical properties of the active ingredient. The fillers may be water insoluble or soluble in water. Examples of the latter include mannitol, sucrose, lactose, dextrose, sorbitol and the like or mixtures thereof. Examples of the former include silicon dioxide, talc, titanium dioxide, alumina, starch, kaolin, microcrystalline cellulose, powdered cellulose, polacrilin potassium, and the like or mixtures thereof. The size of the starter particles and the total solids in the layering formulation will determine the size of the finished pellets.

To form the active core, any suitable apparatus can be used. They include a rotor granulator, pan coater, spheronizer and extruder. In one aspect of the present invention, the core element, including all of its components, are placed into a fluidized bed reactor or apparatus. In this embodiment, the active ingredient and binding agent are applied by placing the starter particles in a fluid bed apparatus, e.g., a fluid bed bottom spray coater, such as, the Wurster coating apparatus (*Pharmaceutical Pelletization Technology,* (1989), pp. 50–54, ed. Isaac Ghebre-Sellassie, Marcel Dekker, Inc., New York and Basel). A solution or suspension of the active ingredient is sprayed on the fluidizing bed of starter particles until the desired amount of drug loading or layering is achieved utilizing methods known in the-art.

The solution or suspension of active ingredient is formed by dissolving or by dispersion of the active ingredient in distilled water or organic solvents used in the art. Antiadherents and binders and other excipients or ingredients as is desirable or appropriate are added to the solution or suspension.

The ratio of active ingredient to starter particle varies according to the unit dosage of drug to be employed and the size of the starting particle. It is apparent that the ratio could vary widely depending on the dosage amount to be employed. For example, it may be desirable or necessary for the finished preparation to consist of a pellet wherein the active ingredient is layered onto a small number of starter particles having a small diameter or wherein the active ingredient is layered more sparingly onto a higher number of starter particles of the same small or a different size diameter starter particle.

Alternatively, the active ingredient, the binding agents and any other components of the core element are mixed together thoroughly and the components are subjected to an extrusion followed by marumerisation to form the core element.

In another embodiment, the active ingredient, binding agent and any other component contained in the core element are provided in a solution or slurry. In this form, the core seeds are sprayed with the solution or slurry. The spraying step may be conducted in any suitable coating equipment. The coating equipment may be a fluidized bed chamber or a rotary fluid bed machine.

Spray coating of the core elements may be undertaken utilizing-bottom, top or tangentially located spray nozzles. A bottom spray nozzle may reside proximate to the base of the fluidized bed facing upwards while a top spraying nozzle is located above the contents of the bed and facing downwards. The spray nozzle may reside in the mid-section of the fluidized bed and be oriented such as to spray tangentially to the rotating core elements.

The core elements formed by whatever method are then subjected to a drying step. The drying step may be conducted in a fluidized bed or drying oven.

Following formation and drying of the pellet, the coating composition of the present invention is applied.

The coating composition of the present invention is coated onto a drug in any conventional form such as a tablet, capsule, pill, granule or powder to form the desired preparation. The composition is employed for coating in the form of an aqueous suspension or aqueous dispersion, such as latex dispersion. The coating composition of the present invention coats the central core element utilizing conventional methods known in the art. For example, the coating composition of the present invention may coat the central core in a fluidized bed or pan. Other examples include spraying or painting the suspension of the composition of the present invention onto the formulation; and immersing the core element suspension of the coating composition of the present invention. Alternatively, the coating composition of the present invention is applied to the core element, e.g., the drug pellets, in fluid bed bottom spray counter by having the pellets suspended in an air stream and an aqueous dispersion of the coating composition is sprayed thereon. Various conventional coating apparatus may be employed to facilitate this including, for example, a centrifugal fluidized bed coating apparatus, a pan coating apparatus, or a fluidized bed granulating coating apparatus.

After the core containing the drug has been coated with the composition of the present invention, the coated pharmaceutical composition (i.e., coating of the present invention and central core) is dried by standard techniques. In the drying step, all or substantially all of the water in the coating composition is removed. For example, the pharmaceutical composition may be dried for about ¼ to about 2 hours at a temperature of from about 30° C. to about 60° C., preferably for about ½ hour at 40° C., and allowed to cool to ambient temperature, and if necessary, sieved through an appropriately sized mesh. Afterwards, the coated pharmaceutical composition of the present invention may be subjected to other conventional procedures, including polishing, sugar coating or additional coating using another coating agent. Also, of course, the solid formulation may be coated with another coating agent prior to the application of the coating composition of the present invention.

As indicated hereinabove, in the present formulation, it is preferred that the active ingredient is provided in a sustained release pellet form. In whatever form, but especially this form, there is significantly less fluctuations in plasma concentration of active ingredients at steady state over a twenty-four hour period, which may allow for less frequent dosing relative to the active ingredient in an uncoated form. Thus, the present formulation is less toxic and has more effective therapeutic activity than an uncoated form.

Similarly, it has been found that the pharmaceutical composition according to the present invention exhibits less diurnal variation in plasma concentrations of active ingredient than prior art preparations; for example, when administered several times on a daily basis.

Without wishing to be bound, it is believed that the coating composition of the present invention is insoluble at an acidic pH, for example, as encountered in the stomach of the patient. Nevertheless, there is some slow release of the active ingredient in the stomach resulting from the drug diffusing through the imperfections inherent in the coating. The slow rate of the release of active ingredient may also be at a relatively constant rate. Without wishing to be bound, it is believed that even at low pH's, a minimal amount of drug may diffuse through the "holes" in the polymer barrier. If the soluble polymer is present, the gastric media will diffuse through the soluble polymer in the coat causing a swelling and slight weakening in the coat, thereby permitting drug to diffuse through the barrier. However, the diffusion of the drug through the coat is slower and more controlled than when the soluble polymer is absent. When the pharmaceutical composition of the present invention enters the intestine, wherein the pH of the intestinal fluid is above 6.0, the enteric polymer present in the coating composition will begin to dissolve upon contact with the intestinal fluid, thereby creating more imperfections or holes in the barrier and permitting contact of the intestinal fluid with the core. When the infiltration into or partial dissolution of the enteric polymer causes the core to contact the solution, the ingredients of the core, including the active ingredient, will begin to diffuse through the solution and into the intestines. As the pharmaceutical composition of the present invention moves through the intestine, more and more of the enteric polymer becomes dissolved, thereby releasing more and more of the active ingredient until eventually the active ingredient is fully released into the intestines. However, this is a slow process. Moreover, the rate of release of the active component into the gastrointestinal tract can be controlled by varying the thickness of the coating of the central core element. For each drug, there is a predetermined or preferred release profile. The practitioner skilled in this art can easily determine the proper thickness of the coat to achieve this desired release profile.

The active ingredient may also be available for absorption even in regions of the gastrointestinal tract which are not sufficiently alkaline to sufficiently solubilize the enteric polymer in the coat.

The term unit dosage form as employed herein refers to physically discrete units suitable as unitary dosages to human subjects and other mammals, each unit containing a predetermined quantity of medicament calculated to produce the desired effect, in association with the other ingredients of the formulation disclosed herein.

In the formulations described hereinabove, the percent of the components are calculated on a dry weight basis, without reference to any water or other components present.

Unless indicated to the contrary, all percentages are weight percentages relative to the pharmaceutical composition.

Moreover, the terms "active ingredient","drug", and "medicament" are used interchangeably.

The singular connotes the plural and vice versa.

The following non-limiting examples further illustrate the present invention. In the following examples, the medicament is illustrated by reference to verapamil hydrochloride. However, this is illustrative only and the present invention is no way restricted thereto.

EXAMPLES

The manufacture of a substrate containing medicaments for the coating is as follows. The substrate can be pellets or tablets or drug particles.

The drug containing pellets is manufactured using the following known techniques:
1. pelletization techniques such as extrusion followed by spheronization or
2. The drug is coated onto inert beads made of sugar or microcrystalline cellulose. The coating can be performed using (a)powder layering techniques using conventional coating pans (b) the rotor process developed by Glatt air techniques using air suspension or (c) air suspension-coating using either a solution or suspension of the drug.

The tablets can be manufactured using commonly known tablet manufacturing techniques.

Verapamil Hcl Controlled Release Beads
Manufacturing Procedure
Step 1. Drug Loading The drug is loaded onto inert spheres, viz., sugar, microcrystalline cellulose, and the like by spraying a drug suspension using air suspension coating techniques.

The drug can be loaded onto the inert spheres using convention pans employing layering technique.

The drug suspension was formulated as follows:

| Ingredient | Typical Formula |
| --- | --- |
| Drug | Verapamil HCl: 1000 grams |
| Binder: Water soluble polymer | Hydroxypropylmethyl cellulose (E5) 40 grams |
| Plasticizer | Polyethylene Glycol 12.5 grams |
| Nonionic surfactant | Polysorbate 80 1 gram |
| Water | QS: 2500 grams |

Step 2: Controlled Release Coating

The beads obtained after the above coating process are coated with an Aqueous latex dispersion of the formulation depicted in the table hereinbelow.

The coating dispersion (polymer dispersion) has a solid content of 5 to 20%.

The pH Independent Polymer

Ethyl cellulose is available as an aqueous latex dispersion containing 25% ethyl cellulose. Two Brands available are Surelease® and Aquacoat®, as 25% aqueous dispersion of ethyl cellulose. If the ethyl cellulose dispersion is not plasticized, as in the case of Aquacoat® (FMC), a plasticizer may be needed. The typical concentration is about 15% of the polymer; however, it can vary from 5% to 25%. Preferred plasticizer are Dibutyl sebacate, Diethel phthalate, Triethyl citrate, and Triacetene.

pH Dependent Polymer

PVAP: Polyvinyl acetate phthalate is available as powder. It is an enteric polymer. The polymer can be added to ethyl cellulose aqueous dispersion as a powder or it can be added as an aqueous solution of said polymer in dilute ammonia. Other alternatives, viz. cellulose acetate phthalate can also be added as a solution in dilute ammonia. Eudgragit L is available as an aqueous dispersion.

Defoamer: Preferably polymethyl siloxane emulsion is utilized in a concentration up to 1%

The following is an example of the typical preparation for the coating composition of the present invention used when verapamil is the active ingredient:

| Component | Concentration Range | Preferred | Alternatives |
| --- | --- | --- | --- |
| Water insoluble Polymer, pH independent | 75 to 100 parts | Ethyl Cellulose 90 parts | Cellulose acetate, Methyl methacrylate polymer Eudragit TL, RS, NE |
| Enteric Polymer | 1 to 25 Parts | PVAP 10 parts | Cellulose acetate phthalate, Eudragit L |
| Water soluble polymer | 0 to 8 parts | hydroxypropyl methyl cellulose 3 parts | HPC, PVP |
| Water | QS 2 to 20% solids | 12% solids | |

The following coatings were tried. Samples were withdrawn during the coating process which represented various coating levels, viz. 5% to 14%.

| Example | Coating Composition | Comments |
| --- | --- | --- |
| Comp. Ex. 1 | 100% PVAP coat up to 14% | High initial release followed by slow release in medium with low pH. Rapid release in pH 7.4 medium |
| Example 1 | Ethyl cellulose 75%, PVAP 20%, HPMC 5%, weight gain 14% | Different release profiles at al pH media, slowest in pH 1.2, then water, then pH 4.5. Very rapid release in pH 7.4 |
| Example 2 | Ethyl cellulose 90%, PVAP 10%, HPMC 3%, weight gain 8%, best 5–6% | Release similar in pH 1.2, 4.5 and water. Rapid release in pH 7.4 |
| Example 3 | Ethyl cellulose 90%, PVAP 10%, weight gain 8%, best 5% | Release similar in pH 1.2, 4.5 and water. Rapid release in pH 7.4 |

EXAMPLES 4–7

| EXAMPLE | COATING COMPOSITION (component by weight) |
|---|---|
| 4* | Ethyl cellulose 90% |
| | PVAP 10% |
| 5 | Ethyl cellulose 85% |
| | PVAP 15% |
| 6 | Ethyl cellulose 88% |
| | PVAP 12% |
| | Xanthan Gum 0.5% |
| 7 | Ethyl cellulose 88% |
| | PUAP 12% |
| | HPMC 0.75% |

*There is no HPMC present in these compositions.

These coating compositions are applied to the verapamil drug suspension, prepared in Examples 1–3.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A composition comprising a core element containing a therapeutically effective amount of a solid medicament and a coating composition on said core element which coating composition comprises a mixture comprising:
   (a) at least 75% by weight of a water insoluble polymer in a latex dispersion in water, said water insoluble polymer being insoluble in both acidic as well as basic pH; and
   (b) 1 to 25% by weight of an enteric polymer which is substantially insoluble in water at a pH below 4.5 and which is substantially soluble in water at a pH above about 6.0, said enteric polymer and said water insoluble polymer being present in an amount effective to control the release of said medicament from the pharmaceutical composition when placed in an aqueous media, said mixture being heterogeneous, wherein the sum of the percentages of said water insoluble polymer and said enteric polymer is equal to or less than 100%.

2. The composition according to claim 1 wherein the water insoluble polymer is present in at least 80% by weight of the coating composition.

3. The composition according to claim 2 wherein the water insoluble polymer is present in at least 85% by weight of the coating composition.

4. The composition according to claim 1 wherein the enteric polymer is present in an amount ranging from about 2 to about 20% by weight of the coating composition.

5. The composition according to claim 1 wherein the enteric polymer is present in an amount ranging from about 5 to about 15% by weight of the coating composition.

6. The composition according to claim 1 wherein weight ratio of the water insoluble polymer to the enteric polymer ranges from about 3:1 to about 15:1.

7. The composition according to claim 6 wherein the ratio ranges from about 4:1 to about 10:1.

8. The coating composition according to claim 1 wherein the water insoluble polymer is present in at least 75% by weight of the coating composition and the enteric polymer is present in an amount ranging from about 2% to about 25% by weight of the coating composition.

9. The composition according to claim 1 wherein the water insoluble polymer is quaternary ammonium methacrylic polymer, an acrylic ester copolymer, a methacrylic ester copolymer or a cellulose ether, cellulose ester or a cellulose ether-ester or a mixture thereof.

10. The composition according to claim 1 wherein the water insoluble polymer is ethyl cellulose, or cellulose acetate or methyl methacrylate polymer.

11. The composition according to claim 1 wherein the enteric polymer is cellulose acetate phthalate, hydroxypropylmethylcellulose phthalate, polyvinyl acetate phthalate, methacrylate copolymer, hydroxy propylmethyl cellulose acetate succinate, hydroxypropylmethylcellulose acetate phthalate, shellac, cellulose acetate trimellitate or a mixture thereof.

12. A sustained release pharmaceutical composition comprising a core element containing a therapeutically effective amount of a solid medicament and a coating composition on said core element, wherein said coating composition is applied to said core element and subjected to drying, said coating composition comprising a mixture comprising:
   (a) at least 75% by weight of a water insoluble polymer in a latex dispersion in water, said water insoluble polymer being insoluble in both acidic as well as basic pH; and
   (b) 1 to 25% by weight of an enteric polymer which is substantially insoluble in water at a pH below 4.5 and which is substantially soluble in water at a pH above about 6.0, said enteric polymer and said water insoluble polymer being present in an amount effective to control release of said medicament from the pharmaceutical composition when in aqueous media, said mixture being heterogeneous, wherein sum of the percentages of said water insoluble polymer and said enteric polymer is equal to or less than 100%.

13. The pharmaceutical composition according to claim 12 wherein the coating composition is present in the pharmaceutical composition in an amount ranging from about 2% to about 25% by weight.

14. A method for the preparation of a sustained release pharmaceutical composition for administration to a patient which comprises forming a core element containing a therapeutically effective amount of a solid medicament and coating said core element with a coating composition comprising a mixture comprising:
   (a) at least 75% by weight of a water insoluble polymer in a latex dispersion in water, said water insoluble polymer being insoluble in both acidic as well as basic pH;
   (b) 1 to 25% by weight of an enteric polymer which is substantially insoluble in water at a pH below 4.5 and which is substantially soluble in water at a pH above about 6.0, said enteric polymer and said water insoluble polymer being present in an amount effective to control release of said medicament from the pharmaceutical composition when placed in an aqueous media, said mixture being heterogeneous, wherein sum of the percentages of water insoluble polymer and enteric polymer is equal to or less than 100%;

and subjecting the coating composition to drying.

15. A method of treating a disease in a patient requiring a sustained release formulation of a medicament for treating said disease, said treatment comprising administering to the patient an effective amount of the pharmaceutical composition of claim 12.

16. The method according to claim 15 wherein the coating composition is present in the pharmaceutical composition in an amount ranging from about 2% to about 25% by weight.

* * * * *